United States Patent
Addington

(10) Patent No.: US 7,402,325 B2
(45) Date of Patent: Jul. 22, 2008

(54) **SUPERCRITICAL CARBON DIOXIDE EXTRACT OF PHARMACOLOGICALLY ACTIVE COMPONENTS FROM *NERIUM OLEANDER***

(75) Inventor: Crandell Addington, San Antonio, TX (US)

(73) Assignee: Phoenix Biotechnology, Inc., San Antonio, TX (US)

( * ) Notice: Subject to any disclaimer, the term of this patent is extended or adjusted under 35 U.S.C. 154(b) by 109 days.

(21) Appl. No.: 11/191,650

(22) Filed: Jul. 28, 2005

(65) Prior Publication Data

US 2007/0026092 A1    Feb. 1, 2007

(51) Int. Cl.
*A61K 36/13*    (2006.01)
(52) U.S. Cl. ...................... 424/770; 424/774
(58) Field of Classification Search .............. None
See application file for complete search history.

(56) References Cited

U.S. PATENT DOCUMENTS

| | | | |
|---|---|---|---|
| 3,833,472 A * | 9/1974 | Yamauchi | 435/99 |
| 4,554,170 A * | 11/1985 | Panzner et al. | 426/651 |
| 5,135,745 A | 8/1992 | Ozel | |
| 5,236,132 A | 8/1993 | Rowley, Jr. | |
| 5,598,979 A | 2/1997 | Rowley, Jr. | |
| 6,517,015 B2 | 2/2003 | Rowley, Jr. | |
| 6,565,897 B2 | 5/2003 | Selvaraj et al. | |
| 6,715,705 B2 | 4/2004 | Rowley, Jr. | |
| 2005/0112059 A1 | 5/2005 | Newman et al. | |

OTHER PUBLICATIONS

Raventos et al, Application and Possibilities of Supercritical Co2 Extration in Good Processing Industry: An Overview, Food Science Tech. Int, 2002, vol. 8, pp. 269-284.*

Lawrence TS. Ouabain sensitizes tumor cells but not normal cells to radiation. Int J Radiat Oncol Biol Phys. Oct. 1988;15(4):953-8.

Manna SK, Sah NK, Newman RA, Cisneros A, Aggarwal BB. Oleandrin suppresses activation of nuclear transcription factor-kappaB, activator protein-1, and c-Jun NH2-terminal kinase. Cancer Res. Jul. 15, 2000;60(14):3838-47.

McConkey DJ, Lin Y, Nutt LK, Ozel HZ, Newman RA. Cardiac glycosides stimulate Ca2+ increases and apoptosis in androgen-independent, metastatic human prostate adenocarcinoma cells. Cancer Res. Jul. 15, 2000;60(14):3807-12.

Mekhail T, Kellackey C, Hutson T, Olencki T, Budd GT, Peereboom D, Dreicer R, Elson P, Ganapathi R, Bukowski R. Phase I study of Anvirzel in patients with advanced solid tumors. Am. Soc. Clin. Oncol. vol. 20 (2001) 82b.

Newman RA, Cisneros A, Felix E, Vijjeswarapu M, Lin Y, Yang P, Azadi P. Composition and preliminary pharmacology studies with Arnvirzel: An extract of *Nerium oleander*. J. Herbal Pharmacotherapy. vol. 13 (2001) 1-15.

Pathak S, Multani AS, Narayan S, Kumar V, Newman RA. Anvirzel, an extract of *Nerium oleander*, induces cell death in human but not murine cancer cells. Anticancer Drugs. Jul. 2000;11(6):455-63.

Raventos M, Durate S, Alarcon R. Application and Possibilities of Supercritical CO2 Extraction in Food Processing Industry: An Overview. Food Sci. Tech. Int. vol. 8 (5) (2002) 269-284.

Verheye-Dua FA, Bohm L. Influence of ouabain on cell inactivation by irradiation. Strahlenther Onkol. Mar. 1996;172(3):156-61.

Verheye-Dua FA, Bohm L. Influence of apoptosis on the enhancement of radiotoxicity by ouabain. Strahlenther Onkol. Apr. 2000;176(4):186-91.

* cited by examiner

*Primary Examiner*—Christopher R. Tate
*Assistant Examiner*—Deborah A. Davis
(74) *Attorney, Agent, or Firm*—Rick Matos; Innovar, L.L.C.

(57) ABSTRACT

A method for the extraction of pharmacologically active components from the oleander plant using supercritical carbon dioxide and combining the extraction with other isolation methods. The extraction is carried out using carbon dioxide at supercritical conditions, with or without the addition of a modifier. The isolated product is recovered in higher yield than with traditional hot water extraction.

19 Claims, No Drawings

SUPERCRITICAL CARBON DIOXIDE EXTRACT OF PHARMACOLOGICALLY ACTIVE COMPONENTS FROM *NERIUM OLEANDER*

BACKGROUND

This invention pertains to the extract of a species of *Nerium*, particularly *Nerium Oleander*, and to a method for production thereof by super critical carbon dioxide extraction.

*Nerium oleander* is an ornamental plant widely distributed in subtropical Asia, the southwestern United States, and the Mediterranean. Its medical and toxicological properties have long been recognized. It has been used, for example, in the treatment of hemorrhoids, ulcers, leprosy, snake bites, and even in the induction of abortion. Oleandrin, an important component of oleander extract, is a potent inhibitor of human tumor cell growth. Oleandrin-mediated cell death is associated with calcium influx, release of cytochrome C from mitochondria, proteolytic processes of caspases 8 and 3, poly (ADP-ribose) polymerase cleavage, and DNA fragmentation.

One extract component of the oleander plant is oleandrin. Oleandrin is a cardiac glycoside that is exogeneous and not normally present in the body. Oleandrin induces apoptosis in human but not in murine tumor cell lines (Pathak et al., *Anti-Cancer Drugs*, vol. 11, pp. 455-463, 2000), inhibits activation of NF-kB (Manna et al., *Cancer Res.*, vol. 60, pp. 3838-3847, 2000), and mediates cell death through a calcium-mediated release of cytochrome C (McConkey et al., *Cancer Res.*, vol. 60, pp. 3807-3812, 2000). A Phase I trial of an oleander extract has been completed recently (Mekhail et al., *Am. Soc. Clin. Oncol.*, vol. 20, p. 82b, 2001). It was concluded that oleander extracts can be safely administered at doses up to 1.2 ml/m$^2$/d. No dose limiting toxicities were found.

In addition to being selectively cytotoxic for tumor cells, cardiac glycosides may also enhance cell response to cytotoxic actions of ionizing radiation. Ouabain, a cardiac glycoside endogeneous to the body, was reported to enhance in vitro radiosensitivity of A549 human lung adenocarcinoma cells but was ineffective in modifying the radioresponse of normal human lung fibroblasts (Lawrence, *Int. J. Radiat. Oncol. Biol. Phys.*, vol. 15, pp. 953-958, 1988). Ouabain was subsequently shown to radiosensitize human tumor cells of different histology types including squamous cell carcinoma and melanoma (Verheye-Dua et al., *Strahlenther. Onkol.*, vol. 176, pp. 186-191, 2000). Although the mechanisms of ouabain-induced radiosensitization are still not fully explained, inhibition of repair from sublethal radiation damage and an increase in radiation-induced apoptosis have been advanced as possibilities (Lawrence, 2000; Verheye Dua et al., 2000; Verheye-Dua et al., *Strahlenther. Onkol.*, vol. 172, pp. 156-161, 1996). The cardiac glycoside oleandrin also has the ability to enhance the sensitivity of cells to the cytotoxic action of ionizing radiation. See U.S. patent application Ser. No. 10/957,875 to Newman, et al.

Extraction of glycosides from plants of *Nerium* species has traditionally been carried out using boiling water. The process of using boiling water as an extraction method to obtain active ingredients from *Nerium oleander* yields many products. Among these are oleandrin, nerine, and other cardiac glycoside compounds. The plant extracts are useful in the treatment of cell-proliferative diseases in animals.

U.S. Pat. No. 5,135,745 to Ozel pertains to extracts of *Nerium* species and their use in the treatment of cell-proliferative diseases. Ozel obtains the extraction of *Nerium oleander* through the use of heat. In particular, sliced plant material is placed in distilled water and boiled until an appropriate density is reached. The mixture is then filtered and heated again.

U.S. Pat. No. 5,869,060 to Selvaraj et al. pertains to extracts of *Nerium* species and methods of production. To prepare the extract, plant material is placed in water and boiled. The crude extract is then separated from the plant matter and sterilized by filtration. The resultant extract can then be lyophilized to produce a powder.

Supercritical fluid extraction involves the use of a supercritical fluid to selectively extract a particular compound. A supercritical fluid is a liquid or a gas at atmospheric conditions, but becomes supercritical when it is compressed above its critical pressure and heated above its critical temperature. Supercritical fluids have increased dissolving power in their supercritical regions. A supercritical fluid exhibits properties between those of a gas and a liquid, and has the capacity to dissolve compounds that may only dissolve poorly or not at all in the gas or liquid state. Supercritical fluids are ideal for extraction of these compounds because they have high dissolving power at high densities and demonstrate good fractionation and separation of the compound from the fluid at lower densities when the pressure or temperature is changed. The general procedure of using supercritical carbon dioxide extraction in food processing industry has been described by Raventos, et al., in 2002 (M. Raventos, et al., Application and Possibilities of Supercritical $CO_2$ Extraction in Food Processing Industry: An Overview, Food Sci Tech Int. Vol. 8 (5) (2002) 269-284), the entire content of which is hereby incorporated by reference.

It has been demonstrated that oleandrin is the principal cytotoxic component of *Nerium oleander* (Newman, et al., *J. Herbal Pharmacotherapy*, vol. 13, pp. 1-15, 2001). Methods to enhance the relative content of oleandrin from plant material are therefore warranted. While hot water extracts of *Nerium oleander* may provide oleandrin and related cardiac glycosides in relatively low yield, an improved method for obtaining a concentrated form of cardiac glycosides including oleandrin is needed.

SUMMARY

The present invention relates to a method for extracting pharmacologically active components from the oleander plant using supercritical carbon dioxide. The method comprises mixing oleander plant starting material with carbon dioxide at a supercritical pressure and temperature, with or without a chemical modifier, then decreasing the pressure and temperature of the mixture and separating out the extract.

The use of powdered oleander leaves as a starting material is preferred. The powdered leaf particles ensure that a maximum amount of surface and internal leaf area is exposed to the extraction process. This provides an exponential increase in the amount of active components that are recovered in the extract, compared to methods of extraction currently available.

DETAILED DESCRIPTION OF PREFERRED EMBODIMENTS

The present invention relates to a method for the extraction of pharmacologically active components from the oleander plant using supercritical carbon dioxide. The extraction is performed using powdered oleander leaves that are mixed with carbon dioxide at a supercritical pressure and temperature, with or without a modifier. The extract is separated as the pressure and temperature of the mixture are decreased.

The preparation of the powdered oleander leaves was carried out according to a specialized processing method described in U.S. Provisional Patent Application Ser. No. 60/653,210. An important component of the method for processing oleander leaves is the use of a patented comminuting and dehydrating system and method which utilizes vortexes of air to extract moisture and separate the plant particles by size. Suitable comminuting and dehydrating systems are described in U.S. Pat. Nos. 5,236,132; 5,598,979; 6,517,015; and 6,715,705, all to Frank Rowley, Jr., and the content of each of these patents is hereby incorporated by reference, described in U.S. Pat. Nos. 5,236,132, 5,598,979, 6,517,015, and 6,715,705 to Rowley, Jr., the entire content of which are hereby incorporated by reference. In general, the method for processing oleander leaves involved collecting suitable leaves and stems, washing the collected plant material, drying the leaves and stems, and passing the leaves through an apparatus which uses vortexes of air to extract moisture and separate the plant particles by size. Larger particles were either re-processed or used as coarse material. The smallest particles were retained as fine oleander dust which can then be subjected to further extraction to obtain oleandrin and other pharmacologically active components.

Supercritical fluid extraction consists of two essential steps: extraction and separation. The starting material is first placed in an extractor device together with the supercritical fluid at specific pressure and temperature conditions. After extraction, the fluid and the compound are passed through a separator which changes the pressure and temperature, thereby reducing the dissolving power of the supercritical fluid and causing the separation or fractionation of the dissolved compound (Raventos, 2002).

Carbon dioxide is a preferred supercritical fluid for the extraction of active components from the oleander plant. Its critical temperature is 31.06° C., its critical pressure is 73.83 bar, and its critical density is 0.460 g/cm$^3$. These critical conditions are all relatively safe and easy to reach, making it appropriate for the extraction of heat labile compounds such as oleandrin. Carbon dioxide is also non-toxic, non-flammable, non-polluting, recoverable, inexpensive, and inert (Raventos, 2002).

In some cases, a co-solvent or modifier can be used in addition to the supercritical fluid. Modifiers have intermediate volatility between the supercritical fluid and the compound being extracted, and they must be miscible with the supercritical fluid. Normally, modifiers are liquids at ambient conditions. Preferred examples of modifiers are ethanol and water (Raventos, 2002). For the extraction of pharmacologically active components from the oleander plant, ethanol is a preferred modifier.

Generally, the first step in the current method of extraction using supercritical carbon dioxide is combining the starting material with the carbon dioxide in an extractor device. In one preferred method, pure $CO_2$ is the supercritical solvent. The $CO_2$ is preferably at a pressure of about 300 bar, or about 30 MPa or about 4350 psi, and a temperature of about 50° C. The ratio of solvent to raw starting material is preferably about 50:1, based on weight of both the solvent and the raw material.

In another preferred method, supercritical carbon dioxide with an ethanol modifier is added to the starting material in an extractor device. The $CO_2$ and ethanol are preferably at a pressure of about 280 bar, or about 28 MPa or 4060 psi, and a temperature of about 50° C. The ratio of solvent and modifier to raw starting material is preferably from about 40 to about 45 to 1, based on the weight of both the solvent and modifier combined and the raw material.

The supercritical solvent, with or without a modifier, in combination with the dissolved starting material, is then passed through a separator device which decreases the pressure and temperature of the solvent mixture until the extract containing the active components is separated and recovered. Once the pressure from the system is released, the supercritical $CO_2$ liquid returns to a gaseous state and is captured as a gas. The extract is a mixture of pharmacologically active compounds, such as oleandrin and other cardiac glycosides, and plant material.

EXAMPLE 1

Extraction of Powdered Oleander Leaves Using Supercritical Carbon Dioxide

Powdered oleander leaves were prepared by harvesting, washing, and drying oleander leaf material, then passing the oleander leaf material through a comminuting and dehydrating apparatus such as those described in U.S. Pat. Nos. 5,236, 132, 5,598,979, 6,517,015, and 6,715,705. The weight of the starting material used was 3.94 kg.

The starting material was combined with pure $CO_2$ at a pressure of 300 bar (30 MPa, 4351 psi) and a temperature of 50° C. (122° F.) in an extractor device. A total of 197 kg of $CO_2$ was used, to give a solvent to raw material ratio of 50:1. The mixture of $CO_2$ and raw material was then passed through a separator device, which changed the pressure and temperature of the mixture and separated the extract from the carbon dioxide.

65 g of extract was obtained as a pure, brownish, sticky, viscous material having a nice fragrance. The color was likely caused by chlorophyll and complex polysaccharides. For an exact yield determination, the tubes and separator were rinsed out with acetone and the acetone was evaporated to give an addition 9 g of extract. The total extract amount was 74 g. Based on the weight of the starting material, the yield of the extract was 1.88%. The content of oleandrin in the extract was calculated using high pressure liquid chromatography and mass spectrometry to be 560.1 mg, or a yield of 0.76%.

EXAMPLE 2

Extraction of Powdered Oleander Leaves Using Supercritical Carbon Dioxide and Ethanol Powdered oleander leaves were prepared by harvesting, washing, and drying oleander leaf material, then passing the oleander leaf material through a comminuting and dehydrating apparatus such as those described in U.S. Pat. Nos. 5,236, 132, 5,598,979, 6,517,015, and 6,715,705. The weight of the starting material used was 3.85 kg.

The starting material was combined with pure $CO_2$ and 5% ethanol as a modifier at a pressure of 280 bar (28 MPa, 4061 psi) and a temperature of 50° C. (122° F.) in an extractor device. A total of 160 kg of $CO_2$ and 8 kg ethanol was used, to give a solvent to raw material ratio of 43.6 to 1. The mixture of $CO_2$, ethanol, and raw material was then passed through a separator device, which changed the pressure and temperature of the mixture and separated the extract from the carbon dioxide.

207 g of extract was obtained after the removal of ethanol as a dark green, sticky, viscous mass obviously containing some chlorophyll. Based on the weight of the starting material, the yield of the extract was 5.38%. The content of oleandrin in the extract was calculated using high pressure liquid chromatography and mass spectrometry to be 1.89 g, or a yield of 0.91%.

EXAMPLE 5

Comparison of Supercritical Carbon Dioxide Extraction to Hot Water Extraction

Hot water extraction is typically used to extract oleandrin and other active components from oleander leaves. Examples of hot water extraction processes can be found in U.S. Pat. Nos. 5,135,745 and 5,869,060.

A hot water extraction was carried out using 5 g of powdered oleander leaves. Ten volumes of boiling water (by weight of the oleander starting material) were added to the powdered oleander leaves and the mixture was stirred constantly for 6 hours. The mixture was then filtered and the leaf residue was collected and extracted again under the same conditions. The filtrates were combined and lyophilized. The appearance of the extract was brown. The dried extract material weighed about 1.44 g. 34.21 mg of the extract material was dissolved in water and subjected to oleandrin content analysis using high pressure liquid chromatography and mass spectrometry. The amount of oleandrin was determined to be 3.68 mg. The oleandrin yield, based on the amount of extract, was calculated to be 0.26%. The Table 1 below shows a comparison between the oleandrin yields for the two supercritical carbon dioxide extractions of Examples 1-2 and the hot water extraction.

TABLE 1

Comparison of Yields

|  | Oleandrin yield based on total extract weight |
|---|---|
| Supercritical Carbon Dioxide Extraction 1 | 0.76% |
| Supercritical Carbon Dioxide Extraction 2 | 0.91% |
| Hot Water Extraction | 0.26% |

As shown in Table 1, the super critical carbon dioxide extractions of oleandrin produced a yield that was several fold higher than that of the hot water extract. Further, after the extraction, the super critical carbon dioxide can be evaporated under mild conditions leaving behind almost no residue.

REFERENCES CITED

The following U.S. Patent documents and publications are hereby incorporated by reference.

U.S. Patent Documents

U.S. Pat. No. 5,135,745 to Ozel
U.S. Pat. No. 5,236,132 to Rowley, Jr.
U.S. Pat. No. 5,598,979 to Rowley, Jr.
U.S. Pat. No. 6,517,015 to Rowley, Jr.
U.S. Pat. No. 6,565,897 to Selvaraj et al.
U.S. Pat. No. 6,715,705 to Rowley, Jr.
U.S. patent application Ser. No. 10/957,875 to Newman et al.

OTHER PUBLICATIONS

Lawrence, T. S., Ouabain sensitizes tumor cells but not normal cells to radiation, *Int. J Radiat. Oncol. Biol. Phys.*vol. 15 (1988) 953-958.

Manna, S. K., N. K. Sah, R. A. Newman, A. Cisneros, B. B. Aggarwal, Oleandrin suppresses activation of nuclear transcription factor-kB, activator protein-1, and c-jun N-terminal kinase, *Cancer Res.* vol. 60 (2000) 3838-3847.

McConkey, D. J., Y. Lin, K. Nutt, H. Z. Ozel, R. A. Newman, Cardiac glycosides stimulate calcium increases and apoptosis in androgen-dependent metastatic human prostate adenocarcinoma cells, *Cancer Res.* vol. 60 (2000) 3807-3812.

Mekhail, T., C. Kellackey, T. Hutson, T. Olencki, G. T. Budd, D. Peereboom, R. Dreicer, P. Elson, R. Ganapathi, R. Bukowski, Phase I study of Anvirzel in patients with advanced solid tumors, *Am. Soc. Clin. Oncol.* vol. 20 (2001) 82b.

Newman, R. A., A. Cisneros, E. Felix, M. Vijjeswarapu, Y. Lin, P. Yang, P. Azadi, Composition and preliminary pharmacology studies with Arnvirzel: An extract of *Nerium oleander, J. Herbal Pharmacotherapy,* vol. 13 (2001) 1-15.

Pathak, S., A. S. Multani, S. Narayan, V. Kumar, R. A. Newman, Anvirzel: an extract of *Nerium oleander* induces cell death in human but not murine cancer cells, *Anti-Cancer Drugs* vol. 11 (2000) 455-463.

Raventos, M., Duarte, S., and Alarcon, R. Application and Possibilities of Supercritical $CO_2$ Extraction in Food Processing Industry: An Overview, Food Sci Tech Int. vol. 8 (5) (2002) 269-284.

Verheye-Dua, F. A., L. Bohm, Influence of cell inactivation by irradiation, *Strahlenther. Onkol.* vol. 172 (1996) 156-161.

Verheye-Dua, F. A., L. Bohm, Influence of apoptosis on the enhancement of radiotoxicity by ouabain, *Strahlenther. Onkol.* vol. 176 (2000) 186-191.

What is claimed is:

1. A method for extracting from powdered oleander leaf a pharmacologically active cardiac glycoside-containing extract useful in the treatment of cell proliferative disease said method comprising:

mixing the powdered oleander leaf with a supercritical carbon dioxide with or without a modifier to give a supercritical solvent mixture, wherein the supercritical carbon dioxide is initially at a pressure above its critical pressure and a temperature above its critical temperature;

decreasing the pressure and temperature of the supercritical solvent mixture to give a separated extract mixture; and recovering the pharmacologically active extract from the separated extract mixture to give the pharmacologically active cardiac glycoside-containing extract useful in the treatment of cell proliferative disease.

2. The method of claim 1, wherein the carbon dioxide is initially at a pressure of about 300 bar and a temperature of about 50° C.

3. The method of claim 1, wherein the supercritical solvent further comprises a modifier.

4. The method of claim 3, wherein the modifier is ethanol.

5. The method of claim 4 wherein the supercritical carbon dioxide and ethanol are initially at a pressure of about 280 bar and a temperature of about 50° C.

6. A method for extracting a pharmacologically active extract useful in the treatment of cell proliferative disease from powdered oleander leaf comprising:

mixing the powdered oleander leaf with supercritical carbon dioxide with or without a modifier to give a supercritical solvent mixture, wherein the supercritical carbon dioxide is initially at a pressure of about 300 bar and a temperature of about 50° C;

decreasing the pressure and temperature of the supercritical solvent mixture to give a separated extract mixture; and recovering the pharmacologically active extract from the separated extract mixture to give the pharmacologically active extract useful in the treatment of cell proliferative disease.

7. A method for extracting a pharmacologically active extract useful in the treatment of cell proliferative disease from powdered oleander leaf comprising:

mixing the powdered oleander leaf with supercritical carbon dioxide to give a supercritical solvent mixture, wherein the supercritical carbon dioxide further comprises ethanol, and wherein the supercritical carbon dioxide is initially at a pressure of about 300 bar and a temperature of about 50° C;

decreasing the pressure and temperature of the supercritical solvent mixture to give a separated extract mixture; and recovering the pharmacologically active extract from the separated extract mixture to give the pharmacologically active extract useful in the treatment of cell proliferative disease.

8. The method of claim 1, wherein the modifier is alcohol and/or water.

9. The method of claim 8, wherein the alcohol is ethanol.

10. The method of claim 1, wherein the pharmacologically active extract comprises oleandrin.

11. The method of claim 1, wherein the oleander leaf is *Nerium oleander.*

12. The method of claim 3, wherein the modifier is alcohol or water.

13. The method of claim 12, wherein the ratio of supercritical carbon dioxide and modifier to oleander plant starting material is about 40:1 to 45:1.

14. The method of claim 1 further comprising drying the oleander leaf prior to mixing with supercritical carbon dioxide.

15. The method of claim 1, wherein the step of decreasing is performed with a separator.

16. The method of claim 7, wherein the ratio of supercritical carbon dioxide to oleander leaf is about 50:1.

17. The method of claim 6, wherein the ratio of supercritical carbon dioxide to oleander leaf is about 50:1.

18. The method of claim 1, wherein the ratio of supercritical solvent to oleander leaf is about 50:1.

19. The method of claim 3, wherein the ratio of supercritical carbon dioxide and modifier to oleander leaf is about 40:1 to 45:1.

* * * * *